United States Patent [19]

Bergeron, Jr.

[11] Patent Number: 4,505,861

[45] Date of Patent: Mar. 19, 1985

[54] METHODS AND INTERMEDIATES FOR THE PREPARATION OF SPERMIDINE, HOMOSPERMIDINE AND NORSPERMIDINE

[75] Inventor: Raymond J. Bergeron, Jr., Gainesville, Fla.

[73] Assignee: University of Florida, Gainesville, Fla.

[21] Appl. No.: 401,387

[22] Filed: Jul. 23, 1982

[51] Int. Cl.$^3$ ............... C07C 121/50; C07C 85/12
[52] U.S. Cl. ................... 260/465 E; 564/491; 564/512
[58] Field of Search ............... 564/491, 512; 260/465 E

[56] References Cited

U.S. PATENT DOCUMENTS 3,280,074  10/1966  McCaleb et al. ............ 564/491 X
4,279,621  7/1981  Reusser ...................... 564/491 X

OTHER PUBLICATIONS

Bergeron et al., J. Org. Chem., vol. 45, p. 1589 (1980).
Bergeron et al., "Reagents for the Selective Acylation of Spermidine, Homospermidine and Bis[3-aminopropyl]-amine", (1981) Synthesis (Int'l Journal of Methods in Synthetic Organic Chemistry).

Primary Examiner—Delbert R. Phillips
Attorney, Agent, or Firm—Dennis P. Clarke

[57] ABSTRACT

Novel azadinitriles and a method for their hydrogenation to produce spermidine, homospermidine and norspermidine.

5 Claims, No Drawings

METHODS AND INTERMEDIATES FOR THE PREPARATION OF SPERMIDINE, HOMOSPERMIDINE AND NORSPERMIDINE

BACKGROUND OF THE INVENTION

In recent years, a great deal of interest has been focused on the naturally occurring acyclic triamines: spermidine [N-3-aminopropyl-N-4-aminobutyl-amine], homospermidine [bis(4-aminobutyl)amine] and norspermidine [bis(3-aminopropyl)amine]. Derivatives of these compounds have been shown to be potent iron chelators [Jacobs et al, Biochem. Biophys. Res. Commun. 74, 16–26 (1977); Tait, Biochem, J., 146, 191 (1975); Peterson et al, Tetrahedron Lett. 1979, 4805 and Ong et al, J. Biol. Chem. 254, 1860 (1979)] and therefore of use in chelation therapy [Hoy et al, Br. J. Haematol. 43, 3 (1979)]. The amines appear in very limited amounts in nature, however, and depend for their ready availability on methods for their synthesis. Methods suggested heretofore for their preparation have proven inefficient and extremely expensive. [Tabor et al, Adv. Enzymol., Vol. 36, p. 203 (1972) and Tabor et al, Annui, Rev. Biochem. Vol. 45, p. 285 (1976)].

It is an object of the present invention to provide efficient and inexpensive methods for the preparation of spermidine, homospermidine and norspermidine in high yields from readily available starting materials.

It is a further object of the present invention to provide novel intermediates useful for the preparation of spermidine, homospermidine and norspermidine.

SUMMARY OF THE INVENTION

The present invention is predicated on the discovery that spermidine, homospermidine and norspermidine can be prepared in an inexpensive and facile manner by hydrogenating 4-benzyl-4-azaoctanedinitrile, 5-benzyl-5-azanonanedinitrile and 4-benzyl-4-azaheptanedinitrile, respectively, in the presence of a catalyst.

The novel intermediates: 5-benzyl-5-azanonanedinitrile and 4-benzyl-4-azaheptanedinitrile may be inexpensively and efficiently prepared by reacting benzylamine with 4-chlorobutanenitrile and acrylonitrile, respectively.

DETAILED DESCRIPTION OF THE INVENTION

Bergeron et al [Journal of Organic Chemistry, Vol. 45, page 1589 (1980)] disclosed a method for preparing 4-benzyl-4-azaoctanedinitrile by reacting benzylamine with acrylonitrile to produce 3-benzylaminopropanenitrile and reacting the latter with 4-chlorobutanenitrile.

Surprisingly, it has been found that benzylamine may be reacted under certain conditions with a 4-halobutanenitrile to produce 5-benzyl-5-azanonanedinitrile in high yield. The bis-alkylation, when carried out according to the present invention, occurs in a higher yield than would normally be expected inasmuch as the expected polyalkylation side reaction is successfully avoided.

The benzylamine is reacted with substantially the stoichiometric amount (i.e., two equivalents) of 4-halobutanenitrile required to react therewith at an elevated temperature and for a time sufficient to produce the dinitrile.

It is preferred to dissolve the 4-halobutanenitrile in a suitable inert, protic organic solvent and add the solution slowly, preferably drop-wise, to a mixture of benzylamine and a base which functions as a scavenger for the hydrogen halide reaction product.

Any suitable protic solvent may be employed in the method of the invention. Preferred solvents include the lower aliphatic alcohols with butanol being the preferred solvent.

An amount of 4-halobutanenitrile in excess of that stoichiometrically required to react with benzylamine to produce the bis-nitrile in the reaction mixture will result in polyalkylation, thereby reducing the overall yield. Although any halo derivative may be employed, it is preferred to utilize the 4-chloro derivative.

The temperature employed for the reaction is not overly critical. An elevated temperature is generally required to drive the reaction to completion in a reasonable length of time. Generally any temperature between 60° and 130° C. may be employed. It is preferred to conduct the reaction at about 115° C.

At a temperature in the above range the reaction is generally complete in from 5 to 30 hours.

The presence of a scavenger for the hydrogen halide reaction product is also necessary to drive the reaction to completion in a reasonable length of time. In the absence of a scavenger the build-up of hydrogen halide in the reaction mixture tends to stop the reaction after a single alkylation. Any conventional hydrogen halide scavenger may be utilized in the method of the invention. Suitable scavengers include the alkali metal and alkaline earth metal carbonates, e.g., $K_2CO_3$, $Na_2CO_3$, etc.

To optimize the yield of the dinitrile, the reaction mixture is preferably refluxed in the absence of oxygen, i.e., in an inert atmosphere (nitrogen, argon) to avoid oxidation of the amines.

The product may be isolated by filtering and washing the salts produced, combining the filtrate and washings and extracting the latter with an acidic solution. The extracts are then made basic and extracted with an organic solvent. The organic phase is dried and the solvent removed to yield the product.

It has also surprisingly been found that benzylamine may be reacted under certain conditions with acrylonitrile to produce 4-benzyl-4-azaheptanedinitrile without comcomitant polymerization. In order to achieve a high yield of easily recoverable product, it is necessary to employ an amount of acrylonitrile in excess of the stoichiometric amount required to react with benzylamine to produce the bis-nitrile product. The utilization of the stoichiometric amount (2 equivalents) results in a low yield of product. Accordingly, it is preferred to employ at least about 2.2 equivalents of acrylonitrile in the reaction mixture. No advantage is realized by employing greater amounts of acrylonitrile.

In order to achieve a reaction between benzylamine and an amount of acrylonitrile in excess of that stoichiometrically required to react with benzylamine to produce the corresponding dinitrile, it is necessary to conduct the reaction in the presence of a free radical scavenger to avoid polymerization of the acrylonitrile. Conducting the reaction in the absence of a free radical scavenger results in a poor yield of the desired product and great difficulty in isolating the product due to the presence of unwanted polymer. Any conventional free radical scavenger, such as catechol, hydroquinone, etc., may be employed in the method of the invention.

The benzylamine and acrylonitrile are preferably heated at an elevated temperature for a time sufficient to complete the reaction. Generally, temperatures in the range of 80° to 170° C., preferably about 140°, are necessary to drive the reaction to completion in about 3 to 9 days.

Inasmuch as the boiling points of the reactants are too low to conduct the reaction at the elevated temperatures at atmospheric pressure, it is preferred to carry out the reaction under autoclave conditions, i.e., in a sealed tube.

The product may be isolated by distillation and further purified by chromatography.

The intermediate, 4-benzyl-4-azaoctanedinitrile may be prepared and isolated according to the method disclosed by Bergeron et al, supra, the disclosure of which is incorporated herein by reference.

The intermediate dinitriles may be converted in one step to the amines as opposed to the inefficient and costly two-step procedure employed heretofore. The conversion may be accomplished in one step in high yields by hydrogenation in the presence of a conventional hydrogenation catalyst. Although any conventional hydrogenation catalyst may be employed, it has been found that optimal yields are produced when employing a noble metal catalyst. Especially preferred, however, is platinum oxide which results in unusually high yields of product.

The amount of catalyst employed is not overly critical. Generally, catalytic amounts in the range of from about 2 to about 30%, preferably 15%, by weight, of the catalyst based on the weight of the nitrile reactant is utilized.

The dinitrile intermediates should be hydrogenated in the presence of an acid in order to avoid condensation or polymerization of the nitriles. Although any acid may be employed, it is generally preferred to utilize an organic acid such as acetic acid. The amines are produced in the form of their acid salts when hydrogenated in the presence of an acid. The free amine may be obtained by dissolving the salt in an aqueous solution, rendering the solution basic (i.e., pH 11) and extracting the free amine with a solvent such as diethyl ether.

The hydrogenation may be conducted at room temperature and the product isolated by dissolving the acid salt of the amine product in water, rendering the solution basic and extracting the amine with a suitable organic solvent.

The invention is illustrated by the following non-limiting examples:

EXAMPLE 1

5-Benzyl-5-azanonanedinitrile was prepared according to the following reaction scheme:

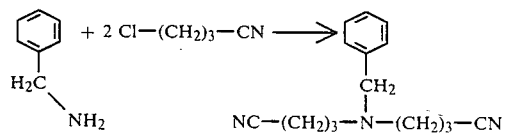

A solution of 4-chlorobutanenitrile (19.3 g, 0.186 mol) in dry butonal (100 ml) was added dropwise over 2 hr to a stirred mixture of benzylamine (10.30 g, 0.096 mol), anhydrous sodium carbonate (30.48 g, 0.288 mol), and potassium iodide (5.66 g, 0.034 mol) at 115° C. After refluxing an additional 20 hr under a nitrogen atmosphere, the mixture was allowed to cool to room temperature and filtered; the salts were washed well with ether. The combined filtrate and washings were extracted with 3 normal hydrochloric acid (3×100 ml) and water (2×100 ml), made basic with sodium carbonate, and extracted with ether (3×100 ml). The resulting ethereal solution was dried with sodium sulfate, filtered, evaporated, and distilled; yield: 15.71 g (70%); b.p. 166° C./0.05 torr. An analytical sample was obtained by column chromatography using petroleum ether/ether (25/75) as eluent.

$C_{15}H_{19}N_3$(241.3): Calc. C 74.65; H 7.94; N 17.41. Found C 74.83; H 8.06; N 17.45.

$^1$H N.M.R. (CDCl$_3$) δ=1.4–2.1 (m, 4H): 2.1–2.8 (m, 8H); 3.50 (s, 2H); 7.22 ppm (s, 5H).

EXAMPLE 2

4-Benzyl-4-azaheptanedinitrile was prepared according to the following reaction scheme:

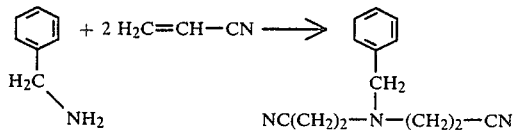

Benzylamine (107.15 g, 1.0 mol) and acrylonitrile (150.2 g, 3.00 mol) were added to a 2000 ml Carius tube which was sealed and heated at 110° C. for 7 days. The reaction mixture was allowed to cool and distilled in vacuo; yield: 87.4 g (41%); b.p. (190° C./0.05 torr. Alternately, the crude reaction mixture was reduced in vacuo and the residue chromatographed on silica gel eluting with diethyl ether to give the product as an oil; yield: 136.50 g (64%, based on 5 g crude material).

$C_{13}H_{15}N_3$(213.3): Calc. C 73.21; H 7.09; N 19.70. Found C 73.29; H 6.94; N 19.65.

H-N.M.R. (CDCl$_3$): δ=2.1–2.5 (m, 4H); 2.6–3.0 (m, 4H); 3.60 (s, 2H); 7.13 ppm (s, 5H).

EXAMPLE 3

4-Benzyl-4-azaheptanedinitrile was also prepared according to the following procedure:

Benzylamine (107.15 g, 1.0 mol), acrylonitrile (150.2 g, 3.00 mol), and hydroquinone (3.0 g, 27.2 mmol) were added to a 2-L Carius tube which was sealed and heated at 140° C. for 7 days. Subsequent distillation provided 202.62 g (95%) of the desired product: b.p. 190° C. (0.05 mm).

EXAMPLE 4

Spermidine was prepared according to the following reaction scheme:

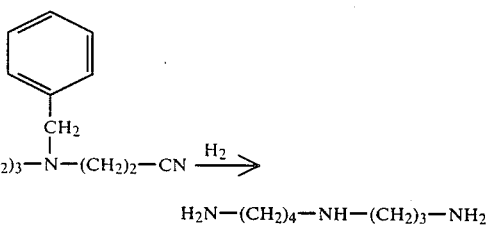

4-Benzyl-4-azaoctanedinitrile (obtained according to the method of Bergeron et al, supra.) (240 mg, 106 mmol) was added to a suspension of platinum oxide (36 mg, 15% by weight) in glacial acetic acid (10 ml) and stirred under a hydrogen atmosphere until no more hydrogen is taken up. The reaction mixture was then filtered through sintered glass and evaporated; yield of 5 triacetate as an oil; 333.5 mg (97%). [The spectral properties of the product thus obtained were identical with those of the triacetate of natural spermidine triacetate].

EXAMPLE 5

The method of Example 4 was repeated utilizing 5-benzyl-5-azanonanedinitrile to obtain homospermidine triacetate in an 85% yield.

EXAMPLE 6

The method of Example 4 was repeated utilizing 4-benzyl-4-azaheptanedinitrile to obtain norspermidine triacetate in an 85% yield.

EXAMPLE 7

One gram of the homospermidine triacetate produced in Example 5 was dissolved in water and potassium carbonate added thereto until the pH of the solution reached 11. The amine was extracted with diethyl ether and the mixture dried over sodium sulfate. The solution was filtered and the solvent removed to yield 0.357 g of oil (82% yield). The NMR spectra of the free homospermidine product are identical with those of the natural product.

EXAMPLE 8

The method of Example 7 was repeated utilizing the norspermidine triacetate produced by Example 6 to produce free norspermidine (84% yield). The NMR spectra of the product are identical to those of the natural product.

EXAMPLE 9

The method of Example 7 was repeated utilizing the spermidine triacetate produced by Example 4 to produce free spermidine (87% yield). The NMR spectra of the product are identical to those of the natural product.

I claim:
1. A method for the preparation of spermidine, homospermidine or norspermidine comprising hydrogenating a member selected from the group consisting of 4-benzyl-4-azaoctanedinitrile, 5-benzyl-5-azanonanedinitrile and 4-benzyl-4-azaheptanedinitrile in the presence of a catalytic amount of a noble metal containing hydrogenation catalyst and an acid.
2. The method of claim 1 wherein said catalyst is platinum oxide.
3. The method of claim 1 wherein said acid is an organic acid.
4. The method of claim 1 wherein said acid is acetic acid.
5. The method of claim 1 for preparing spermidine wherein said 4-benzyl-4-azaoctanedinitrile is prepared by reacting benzylamine with acrylonitrile to produce 3-benzylaminopropanenitrile and reacting the latter with 4-halobutanenitrile.

* * * * *